United States Patent
Walsh et al.

(10) Patent No.: US 6,649,384 B2
(45) Date of Patent: Nov. 18, 2003

(54) SYSTEM AND METHOD FOR ENCAPSULATING BIOLOGICAL MATERIAL BY APPLYING ELECTROSTATIC CHARGE TO CAPSULES

(75) Inventors: Stephen E. Walsh, North Oaks, MN (US); Monte R. Canfield, Center City, MN (US); Nancy J. Drake, Vadnais Heights, MN (US)

(73) Assignee: Islet Technology, Inc., St. Paul, MN (US)

(*) Notice: Subject to any disclaimer, the term of this patent is extended or adjusted under 35 U.S.C. 154(b) by 0 days.

(21) Appl. No.: 09/900,466

(22) Filed: Jul. 5, 2001

(65) Prior Publication Data

US 2002/0022016 A1 Feb. 21, 2002

Related U.S. Application Data

(60) Provisional application No. 60/215,947, filed on Jul. 5, 2000.

(51) Int. Cl.[7] .......................... C12N 21/10; C12N 11/04; C12N 5/00; A61F 2/00; C12M 1/00
(52) U.S. Cl. ...................... 435/178; 424/423; 424/93.7; 435/182; 435/382; 435/395; 435/283.1
(58) Field of Search .................................. 435/177, 178, 435/182, 382, 395, 283.1; 424/423, 93.7

(56) References Cited

U.S. PATENT DOCUMENTS

| | | | |
|---|---|---|---|
| 3,160,686 A | 12/1964 | Doyle et al. | 264/4 |
| 3,313,608 A | 4/1967 | Guyer et al. | 65/21 |
| 4,352,883 A | 10/1982 | Lim | 435/178 |
| 4,391,909 A | 7/1983 | Lim | 435/178 |
| 4,407,957 A | 10/1983 | Lim | 435/178 |
| 4,409,331 A | 10/1983 | Lim | 435/178 |
| 4,663,286 A | 5/1987 | Tsang et al. | 435/178 |
| 4,673,566 A | 6/1987 | Goosen et al. | 424/19 |
| 4,689,293 A | 8/1987 | Goosen et al. | 435/1 |
| 4,696,286 A | 9/1987 | Cochrum | 128/1 R |
| 4,789,550 A | 12/1988 | Hommel et al. | 424/493 |
| 4,803,168 A | 2/1989 | Jarvis, Jr. | 435/178 |
| 4,806,355 A | 2/1989 | Goosen et al. | 424/424 |
| 4,956,128 A | 9/1990 | Hommel et al. | 264/4 |
| 5,227,298 A | 7/1993 | Weber et al. | 435/178 |
| 5,260,002 A | 11/1993 | Wang | 264/4.1 |
| 5,286,495 A | 2/1994 | Batich et al. | 424/490 |
| 5,429,821 A | 7/1995 | Dorian et al. | 424/424 |
| 5,462,866 A | 10/1995 | Wang | 435/174 |
| 5,470,731 A | 11/1995 | Cochrum | 435/182 |
| 5,514,377 A | 5/1996 | Cochrum et al. | 424/423 |
| 5,521,079 A | 5/1996 | Dorian et al. | 435/174 |
| 5,531,997 A | 7/1996 | Cochrum | 424/424 |
| 5,578,314 A | 11/1996 | Cochrum et al. | 424/424 |
| 5,639,467 A | 6/1997 | Dorian et al. | 424/422 |
| 5,643,594 A | 7/1997 | Dorian et al. | 424/424 |
| 5,648,099 A | 7/1997 | Batich et al. | 424/497 |
| 5,656,468 A | 8/1997 | Dorian et al. | 435/178 |
| 5,679,565 A | 10/1997 | Mullen et al. | 435/260 X |
| 5,693,514 A | 12/1997 | Dorian et al. | 435/178 |
| 5,876,742 A | 3/1999 | Cochrum et al. | 424/424 |
| 6,001,387 A | 12/1999 | Cochrum | 424/424 |
| 6,020,200 A | 2/2000 | Enevold | 435/382 |
| 6,033,888 A | 3/2000 | Batich et al. | 435/178 |

OTHER PUBLICATIONS

*Electrostatically Produced Fuel Sprays for Combustion Applications*, W. Balachandran, D. Hu, A.J. Yule, J.S. Shrimpton, A.P. Watkins, International Conference Liquid Atomization and Spraying Systems –94, Rouen, France, pp. 994–1001, Jul. 1994.

*A Comparison of Four Solutions for Cold Storage of Pancreatic Islets*, V.D.A. Delfino, D.W.R. Gray, C. Kar Leow, S. Shimizu, D.J.P. Ferguson, P.J. Morris, Official Journal of the Transplantation Society, vol. 56, No. 6, pp. 1325–1330, Dec. 1993.

*The Electrical Dispersion of Liquids as Aerosols*, V.G. Drozin, Journal of Colloid Science, vol. 10, pp. 158–164, 1955.

*Ligament Formation for an Electrostatic Atomizer Operating in Multi–jet Mode*, J.T. Epperson, P.E. Sojka, Proceedings of the 12th Annual Conference on Liquid Atomization and Spray Systems, Indianapolis, Indiana, pp. 231–235, May 1999.

*Performance of Vaned–Disk Atomizers*, W.H. Herring, Jr., W.R. Marshall, A,I,Ch,E, Journal, vol. 1, No. 1, pp. 200–209, Jun. 1955.

*Atomization of Liquids by Means of Rotating Cup*, J.O. Hinze, H. Milborn, Journal of Applied Mechanics, vol. 17, No. 2, pp. 145–153, Jun. 1950.

*Low Charge Density Electrostatic Atomization*, A. Kelly, IEEE Transactions on Industry Applications, vol. IA–20, No. 2, 267–273, Mar./Apr. 1984.

(List continued on next page.)

Primary Examiner—David M. Naff
(74) Attorney, Agent, or Firm—Patterson, Thuente, Skaar & Christensen, P.A.

(57) ABSTRACT

A method and system for the effective and consistent encapsulation of viable (i.e., living or physiologically active) biological material (preferably, pancreatic islets also known as islets of Langerhans) with a polymeric material (preferably, a biocompatible semipermeable alginate) to form a gelled capsule, which preferably can be transplanted into genetically dissimilar hosts. The method includes an electrostatic mixing process for producing encapsulated cell clusters with at least two polymeric coatings, and the system includes an improved spinning disk atomizer. In an embodiment, biological material is encapsulated in a first alginate layer, the resultant capsules are suspended in a liquid carrier medium such as a saline solution, an electrostatic charge is applied to the carrier medium which is then introduced into an alginate solution, and the resultant suspension is atomized and gelled to form a second alginate layer.

30 Claims, 8 Drawing Sheets

OTHER PUBLICATIONS

Figure 1:
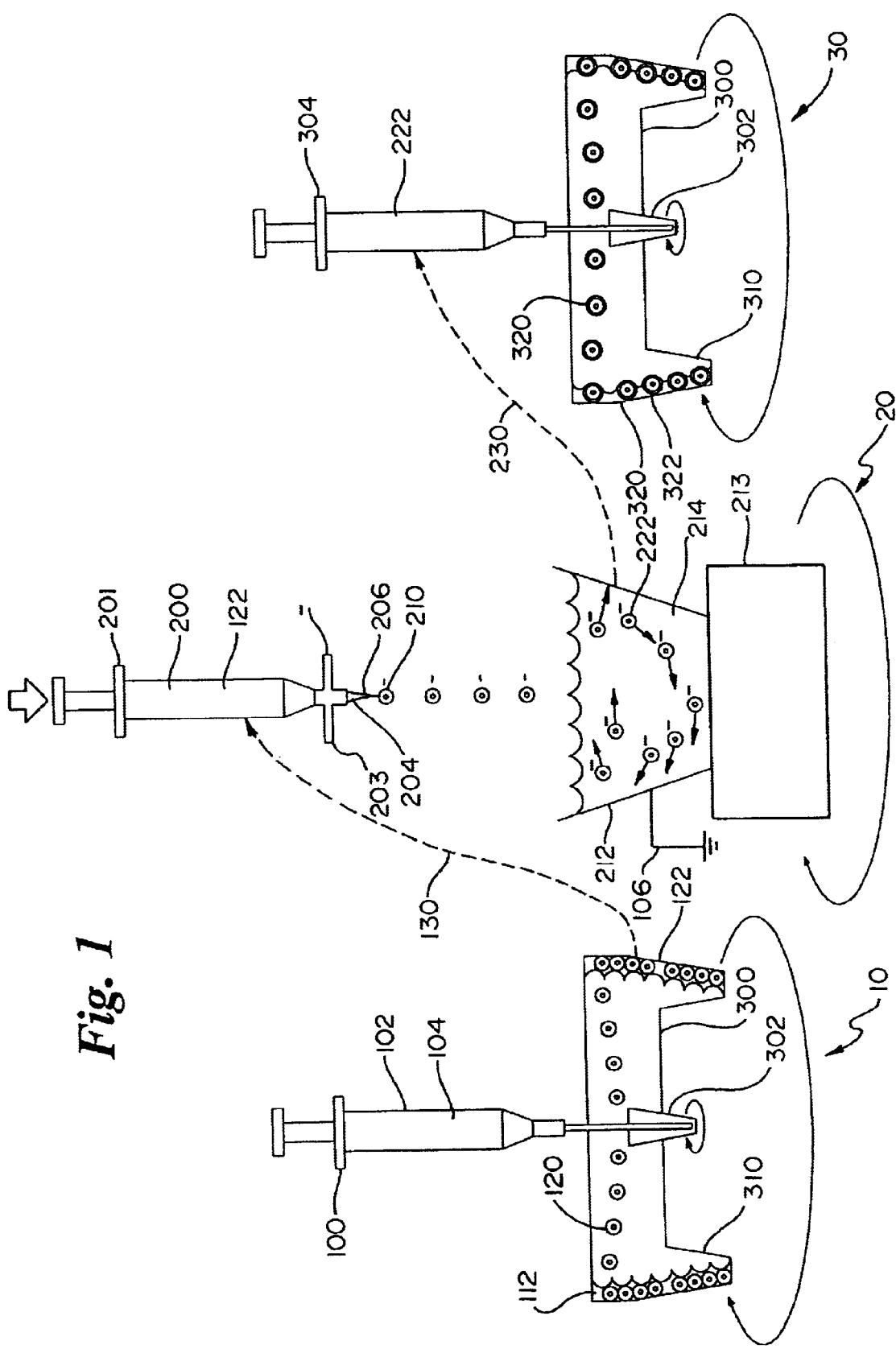

*Atomization of Emulsions by Spinning Disks in the Ligament Formation Mode*, Y. Kitamura, S. Ide, T. Takahashi, Proceedings of the 4th International Conference on Liquid Atomization and Spray Systems, Sendai, Japan, pp. 317–323, Jul. 1988.

*Some Investigations on the Deformation and Breaking of Water Drops in Strong Electric Fields*, W.A. Macky, Proceedings of the Royal Society of London, Series A, vol. 133, pp. 565–587, Oct. 1931.

*Film Thickness of a Bingham Liquid on a Rotating Disk*, S. Matsumoto, Y. Takashima, A. Kayano, Y. Ohta, T. Kamiya, Industrial & Engineering Chemistry Fundamentals, vol. 21, No. 3, pp. 198–202, Aug. 1982.

*Atomization Characteristics of Power Law Fluids by Rotating Disks*, S. Matsumoto, Y. Takashima, Proceedings of The 1st International Conference on Liquid Atomization and Spray Systems, The Fuel Society of Japan, pp. 145–150, Aug. 1978.

*Dynamics of Drop Formation in an Electric Field*, P. K. Notz, O.A. Basaran, Proceedings of the 11th Annual Conference on Liquid Atomization and Spray Systems, Sacramento, CA, pp. 180–184, May 1998.

*On the Instability of Jets*, Lord Rayleigh, F.R.S., Proceedings of the London Mathematical Society, vol. 10, pp. 4–13, Nov. 1878.

*The Theory of Sound*, J.W. Strutt, Baron Rayleigh, F.R.S., vol. 2, Dover Publications, pp. 351–355, 1945.

*Metabolic Control After Autotransplantation of Highly Purified Canine Pancreatic Islets Isolated in UW Solution*, M.P.M. van der Burg, O.R. Guicherit, R.J. Ploeg, M. Flölich, J.A. Bruijn, J.P. Scherft, H.G. Gooszen, Transplantation Proceedings, vol. 23, No. 1, pp. 785–786, Feb. 1991.

*Comparative Study of Microencapsulated Rat Islets Implanted in Different Diabetic Models in Mice*, S. Darquay, D. Chicheportiche, F. Capron, C. Boitard, G. Reach, Hormone and Metabolism Research, Supplement Series vol. 25, pp. 209–213, 1990.

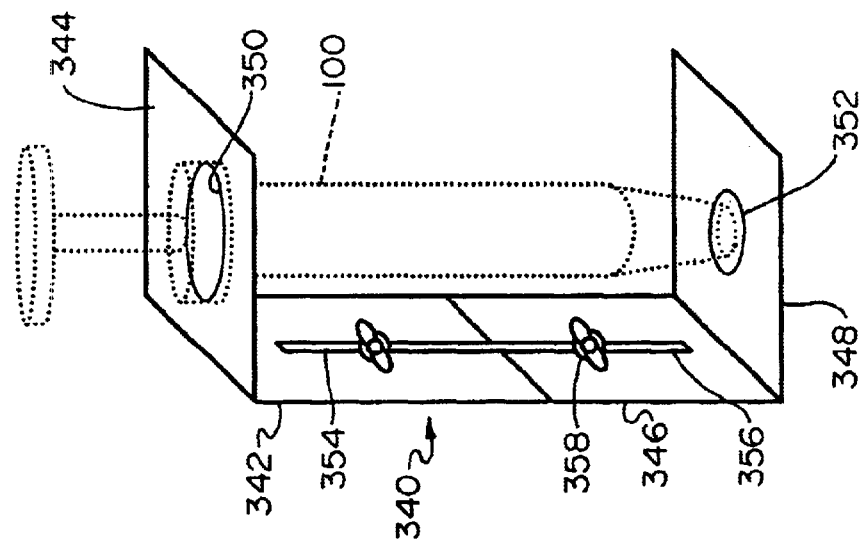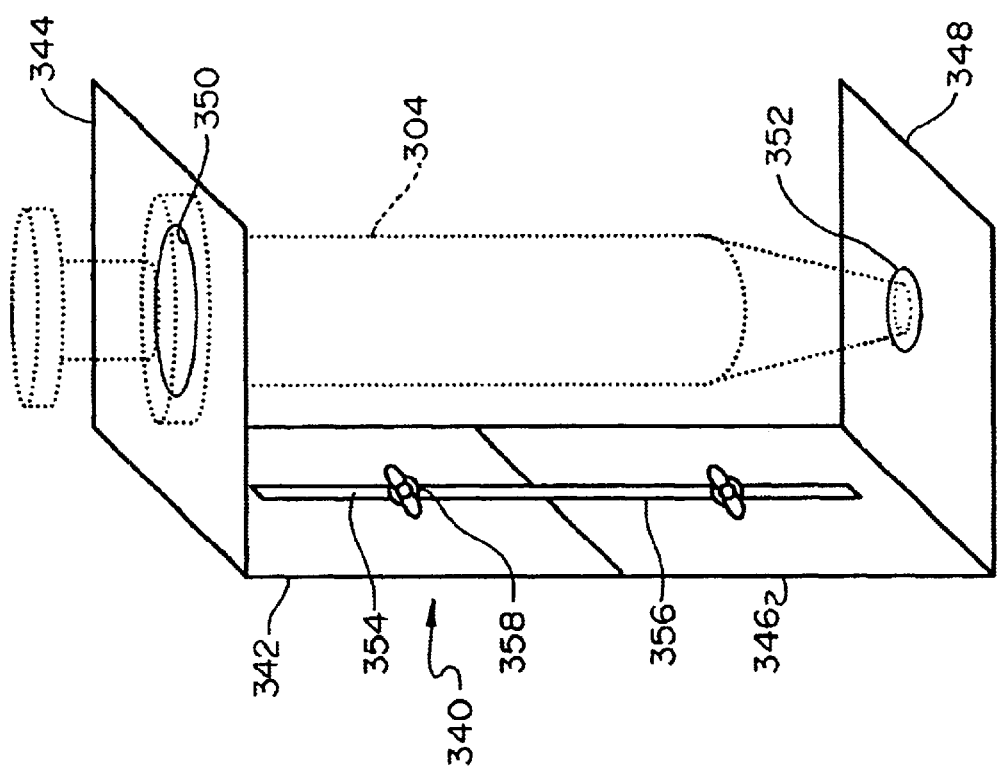

SYSTEM AND METHOD FOR ENCAPSULATING BIOLOGICAL MATERIAL BY APPLYING ELECTROSTATIC CHARGE TO CAPSULES

PRIORITY APPLICATION

This application claims benefit of U.S. Provisional Patent Application Ser. No. 60/215,947, filed Jul. 5, 2000, which is incorporated herein by reference.

FIELD OF THE INVENTION

This invention describes a method and system for the consistent and effective encapsulation of viable biological material (e.g., individual living cells, cell clusters, or organ tissue) with a polymeric coating material.

BACKGROUND OF THE INVENTION

Transplantation of organ tissue (e.g., pancreatic islets) into genetically dissimilar hosts has gained a significant interest in the treatment for functional deficiencies of secretory and other biological organs. Transplantation, however, generally requires the continuous use of immunosuppressive agents by the transplant recipient in order to forestall rejection of the transplanted tissue by the recipient's immune system. Unfortunately, these immunosuppressive agents can deprive the recipient of adequate protective immune function against diseases.

A potential solution that avoids the need for such immunosuppressive agents is the encapsulation of the tissue material so as to protect the transplanted tissue from the recipient's immune system. Encapsulation generally eliminates the need for immunosuppressive agents to prevent adverse immune system response and rejection of the implant. Encapsulation with a sufficiently semi-permeable protective barrier coating not only generally prevents an immune response, but also provides for diffusion of oxygen into the encapsulated material along with the transfer of nutrients, ions, glucose, and hormones, as well as the excretion of metabolic waste. This maintains the health of the encapsulated tissue material.

One promising approach for the encapsulation of tissue material such as pancreatic islets involves the use of coatings formed of a non-fibrogenic alginate, a gelatinous substance that can be derived from certain kinds of kelp. The islets are suspended in a viscous, liquid alginate, which is then atomized by any of a number of different arrangements into droplets of suitable size to encapsulate the islets. Once the droplets come into contact with a gelling solution, such as calcium chloride or barium chloride, a single layer alginate coating is created around the islets. Examples of this approach for creating single layer alginate coatings using an electrostatic coating process are shown in U.S. Pat. No. 4,789,550 (Hommel et al.), U.S. Pat. No. 4,956,128 (Hommel et al.), U.S. Pat. No. 5,429,821 (Dorian et al.), U.S. Pat. No. 5,639,467 (Dorian et al.), U.S. Pat. No. 5,656,468 (Dorian et al.) and U.S. Pat. No. 5,693,514 (Dorian et al.). An example for creating a single layer alginate coating using an air knife process is shown in U.S. Pat. No. 5,521,079 (Dorian et al.). A pressurized process for coating droplets is described in U.S. Pat. No. 5,260,002 (Wang) and U.S. Pat. No. 5,462,866 (Wang). Other examples for creating a single layer alginate coating using a spinning disk arrangement are shown in U.S. Pat. No. 5,643,594 (Dorian et al.) and U.S. Pat. No. 6,001,387 (Cochrum). Examples for creating a single layer alginate coating using a piezoelectric nozzle are shown in U.S. Pat. No. 5,286,496 (Batich et al.), U.S. Pat. No. 5,648,099 (Batich et al.) and U.S. Pat. No. 6,033,888 (Batich et al.)

A problem common to all of these techniques for creating single layer alginate coatings is the formation of non-encapsulated or partially encapsulated islets. Any non-encapsulated biological material or capsules that are only partially coated or that have too thin of a coating will lead to an adverse immunological response when transplanted into the recipient. One way to decrease this problem is to increase the diameter of the single coating so that the capsules have diameters in the range of 700–800 microns. Unfortunately, these large-sized capsules tend to be less effective when transplanted into a recipient because the larger diameter diminishes the ability of oxygen to penetrate completely into the interior of the capsule. It has also been found that large-sized capsules tend to increase the potential for macrophage attack by the recipient's immune system and can limit the potential transplantation sites as compared to smaller-sized capsules.

It has been discovered that encapsulation of tissue material such as pancreatic islets with a second coating of a cross-linkable polymer can provide substantially complete coverage of the islets in order to minimize or eliminate the possibility of adverse immune reactions, while at the same time providing a capsule having a dimension on the order of 400–500 microns. The multiple coatings of the individual capsules containing the core of living tissue serve as an additional means for assisting in the resistance to chemical, mechanical, or immune destruction by the host. The smaller-sized capsule is believed to permit oxygen to better permeate into the interior of the capsule as oxygen can normally permeate up to about 200–250 microns into encapsulated tissue material.

U.S. Pat. No. 5,470,731 (Cochrum) and U.S. Pat. No. 5,531,997 (Cochrum) describe a double layer coating for tissue that comprises a first layer of a gellable organic polymer and a cationic polymer and a second water-soluable, semi-permeable layer chemically bonded to the first layer. U.S. Pat. No. 6,020,200 (Enevold) describes a dual layer coating having a stabilized outer layer formed of a cross-linked polmer matrix. U.S. Pat. No. 5,227,298 (Weber at al.) describes a double walled alginate coating. U.S. Pat. No. 5,578,314 (Cochrum et al.) teaches such a method for applying multiple layers of alginate onto biological material (e.g., pancreatic islets). In this method, a first layer of a multiple layer alginate coating is applied using a solution of an alginate containing a high ratio of guluronate to manuronate, and the second layer is applied using a solution of an alginate containing a high ratio of mannuronate to guluronate. U.S. Pat. No. 5,876,742 (Cochrum et al.) teaches a multiple layer alginate coating where an intermediary halo layer of a soft gel is formed between the inner and outer alginate coating layers.

While the use of multiple layer alginate coatings solves many of the problems associated with single layer coatings, the existing techniques for generating such multiple layer alginate coatings are not well suited to large scale manufacturing systems that can consistently and reliably produce large amounts of encapsulated material. In order to obtain large amounts of encapsulated islets, for example, necessary for a single human transplantation procedure, as many as 500,000 to 1,000,000 encapsulated islet equivalents (one islet equivalent is equal to a cell cluster of islets having a diameter of 150 microns), or at least 8000 islet equivalents per kilogram of body weight may be required.

Several problems with the existing techniques have generally prevented the large-scale manufacture of encapsulated islets to meet these needs. First, the existing techniques tend to generate a very large number of empty capsules or "blanks". While such blanks can be created in either the first coating process or the second process, the problem is most noticeable where a droplet is produced during the second coating process that does not contain an islet. Second, the existing techniques also tend to create encapsulated islets in which multiple single coated islets either stick together during the coating process or end up with more than about ten islets being contained within the same second coating encapsulation, conditions which are referred to as "clumping". When clumping occurs during the coating process, the entire batch of capsules being processed can be destroyed. Single-coated capsules can bind together into clumps that are subsequently coated a second time during the encapsulation process. Depending upon the number of single-coated capsules in a particular clump, the coated clumps do not function as effectively as a double-coated capsule containing only one or up to four single-coated capsules, most likely because the size of the resultant capsule of clumped single-coated capsules is too large.

Most importantly, the entire encapsulation process for biological materials is a time and stress sensitive process. The longer that living tissue or cells are exposed to the process or the stresses created by the encapsulation process, the less viable and effective the resulting encapsulated tissue material will be. Moreover, it has been discovered that encapsulated islet cells, for example, have a limited viability of only a few days in cell culture, both prior to encapsulation and after encapsulation and prior to transplantation. The existing techniques for double alginate coating have been limited to processing relatively small batches of cell clusters, on the order of only tens of thousands of islets per batch. Even with these small batches, the process can take several hours, exposing the cells to stress during the entire period of the coating process. The ability to process only small batches of islets requires the encapsulation process to be repeated numerous times in order to obtain the requisite number of islets for a single transplantation, thereby potentially extending the time that the encapsulated islets must be maintained in cell culture prior to transplantation. Small batches are also inefficient in that a certain number of the islets will be lost during each process. When small batches are processed, the number of islets lost represents a larger percentage of the total islets processed than if larger batches could be processed.

Although multiple layer alginate coatings for encapsulating tissue material have offered promise as a potential alternative for protecting tissue implants without the use of immunosuppressive agents, the existing techniques are not well-suited for the large-scale manufacturing required to generate the necessary volume of encapsulated tissue material in a short period of time for a successful transplant operation. It would be desirable to provide for a manufacturing method and system for the consistent and effective encapsulation of large batches of biological material that can overcome these limitations.

SUMMARY OF INVENTION

A method and system for the consistent and effective encapsulation of large batches of biological material applies an electrostatic charge to capsules having a first layer coating prior to creating a second layer coating so as to singulate and separate the single coated capsules during a mixing process prior to the second layer coating process. The single layer coated capsules are suspended in a liquid carrier medium for purposes of applying the electrostatic charge. Preferably, the liquid carrier medium is low viscosity and physiologically balanced to the biological material. The electrostatically charged carrier medium with the single layer coated capsules is then introduced into an alginate solution as part of a mixing process performed prior to the second layer coating process. Preferably, both the first layer coating process and the second layer coating process utilizes a spinning disk encapsulation apparatus having a central cup with at least one groove in an interior surface that causes droplets to exit from the center cup into an outer collection chamber containing a gelling solution in one or more relatively well-defined singulated lines.

In a preferred method of the present invention, cell clusters of biological material are suspended in a first alginate solution to form a first alginate suspension. Droplets are formed from the first alginate suspension, with at least some of the droplets containing cell clusters. The droplets are then gelled to form capsules having a first layer coating surrounding at least a portion of the cells. These single coated capsules are suspended in a liquid carrier medium that is preferably low viscosity and physiologically balanced to the biological material to form a carrier suspension. An electrostatic charge is applied to the carrier suspension prior to introducing the carrier suspension into a second alginate solution to create a singulated flowstream of the carrier suspension containing the single-coated capsules. As part of the mixing process, the second alginate solution is agitated by a vortex mixer as the singulated flowstream of the carrier medium containing the single-coated capsules is introduced into the second alginate solution to create a second alginate suspension. As a result of the process of applying the electrostatic charge and agitating the second alginate solution, the capsules do not clump as they are introduced into the second alginate solution to create the second alginate suspension. After this mixing process is complete, the second alginate suspension containing the separated single-coated capsules are formed into droplets and then gelled to form a second layer coating around the capsules.

In a preferred system of the present invention, a series of apparatus and processing techniques are arranged to effectively and consistently encapsulate biological material. The system includes a system for atomizing a first alginate suspension containing cell clusters of the biological material in a first alginate solution to form droplets, the majority of the droplets containing at least one cell cluster. The droplets are gelled in order to form single-coated capsules having a first layer coating surrounding at least a portion of the cell clusters. The single coated capsules are placed in a liquid carrier medium for the purpose of applying the electrostatic charge prior to the second layer coating process. Preferably, a conductive collar is used for applying the electrostatic charge to the liquid carrier medium containing the single-coated capsules. As the carrier medium containing the single-coated cells is introduced into a second alginate solution to create a second alginate suspension, the electrostatic charge separates the single-coated capsules in a fluid stream of the carrier medium. The second alginate solution is agitated by a vortex mixer as the carrier medium is introduced. Together, the electrostatic charge and the agitation of the second alginate solution prevent the single-coated capsules from clumping together in the second alginate solution as the second alginate suspension is formed. After this mixing process is complete, a system for atomizing and gelling the separated capsules in the second alginate suspension is used to form a second layer coating around the capsules.

Preferably, the system for atomizing and gelling droplets to create both the first and second layer coatings is a spinning disk encapsulation apparatus having a center cup into which droplets of the appropriate alginate suspension are introduced and an outer collection chamber containing a gelling solution for gelling the droplets of the alginate suspension so as to form a layer coating around the capsules. In order to achieve more effective operation for the coating process, the center cup preferably includes at least one groove defined on an inner wall of the center cup. When the droplets of the alginate suspension are introduced into the center cup, the grooves cause the droplets to travel from the center cup into the outer collection chamber in one or more relatively well-defined singulated lines exiting from the center cup. A singulated line is a line of moving liquid and/or droplets that does not mingle with other lines. The grooves in the central cup provide the ability to control the location of the singulated lines of droplets, as well as the uniformity of the size and shape of the droplets created by the spinning disk encapsulation apparatus.

The present invention overcomes the problem of clumping that has traditionally been associated with scaling up the coating of biological material and reduces the problems of blanks created in the second coating process. The challenge of successfully mixing and double coating living tissue in large quantities without damaging the tissue is complex. Single coated capsules suspended in a second alginate solution behave somewhat like tapioca beads in pudding. Mixing or stirring with mechanical mixing techniques to disperse the capsules in the second alginate solution is either ineffective because the mixing is not vigorous, or is damaging to the tissue material because the mixing is too vigorous. If the viscosity of the second alginate solution is reduced or if the volume is increased so as to more easily mechanically mix the capsules, the effectiveness of the subsequent coating process is effected and the number of blanks produced in the droplet generation stage of the subsequent coating process increases significantly. The present invention recognizes that the way to avoid the clumping problem is to utilize a mixing process that avoids clumping in the first place by singulating and separating the single-coated capsules such that the capsules do not touch one another as they are introduced into the second alginate solution.

Specifically, the present invention provides a method and system for the effective and consistent encapsulation of viable (i.e., living or physiologically active) clusters of biological material (preferably, pancreatic islets also known as islets of Langerhans) with a polymeric material preferably, a biocompatible semi-permeable alginate) to form a gelled capsule, which can be transplanted into genetically dissimilar hosts. At least two layers of polymer (e.g., alginate) are applied. With the current invention, the failures and defects in the previously described methods are eliminated and it is possible to produce high quality double layer capsules in high volumes, while minimizing the processing time and stress for the biological material being encapsulated. Unlike existing double layer alginate encapsulation techniques, the present invention allows for double layer encapsulation of all of the cell clusters from a donor organ as part of one large-scale batch process. In contrast to existing techniques which typically produce blanks during the second coating process at a ratio of at least 10:1 to encapsulated cells, and more commonly at a blank ratio of 50:1, the present invention produces blanks during the second coating process at a ratio of less than 10:1 and more typically at a blank ratio of 6:1 or better.

One embodiment of a method of the present invention includes providing a composition that includes a liquid carrier medium and polymeric capsules that include biological material in a first polymeric coating; applying an electrostatic charge to the composition of carrier medium and polymeric capsules; producing a flowing stream of droplets of the composition, wherein a relatively high proportion of the droplets include the polymeric capsules; and introducing the flowing stream of droplets directly into a second polymeric coating composition to form a suspension. These steps form the electrostatic mixing process described in greater detail below. Preferably, the method subsequently includes atomizing and contacting the suspension with a gelling solution to gel the second polymeric coating composition and encapsulate the polymeric capsules having a first polymeric coating in a second polymeric coating. This process can be used to provide one or more polymeric coatings to biological material by repeating the steps of applying an electrostatic charge, introducing the flowing stream of droplets into a polymeric coating composition to create a suspension, and atomizing and contacting the suspension with a gelling solution.

This step of introducing the single-coated material (i.e., single-coated capsules, which are the polymeric capsules that include biological material in a first polymeric coating) into the second polymeric coating composition using an electrostatic charge is not carried out in conventional methods. Typically, in conventional methods the single-coated capsules are simply mixed with the second polymeric coating composition by mechanical means. In conventional methods, this suspension of single-coated capsules is then atomized by electrostatic charge or other means and collected in a gelling solution (as opposed to a polymeric coating composition). The step of the present invention of dispersing the single-coated capsules into the second polymeric coating composition using an electrostatic mixing process provides significant advantage in that it reduces the aggregation and clumping of the single-coated capsules and enhances the yield of the double-coated capsules (i.e., the capsules with a first and second polymer coating).

A preferred embodiment of the present invention is used for encapsulating pancreatic islets, although the present invention is equally applicable to encapsulation of clusters of other cells ranging in size from single cells to cell clusters as large as several hundred microns. When used with pancreatic islets, the carrier medium is a physiological saline solution and the polymeric capsules including pancreatic islets in a first polymeric coating preferably include an alginate. An electrostatic charge at a voltage of about 1 kV to about 100 kV (preferably, 5 kV to 30 kV) is applied to the composition of the carrier medium and the polymeric capsules containing the pancreatic islets to create an electrostatic charge on a flowing stream of droplets of the composition, wherein a relatively high proportion of the droplets include pancreatic islet clusters. The flowing stream of droplets is introduced directly into a second polymeric coating composition contained in a vortex mixer to form a suspension. This suspension is then atomized and gelled by introducing the suspension into an encapsulation apparatus including a spinning disk atomizer and an outer collection chamber that includes a gelling solution to gel the second polymeric coating composition and encapsulate the polymeric capsules in a second polymeric coating, which includes an alginate.

The preferred embodiment of the spinning disk atomizer includes a central cup having an opening; a reservoir portion; at least one inner wall portion connecting the reservoir portion to the opening; and at least one groove formed in the inner wall portion. Preferably, the at least one groove extends substantially between the reservoir portion and the opening. The preferred embodiment of the spinning disk atomizer directs the path of travel of the capsules from the center cup into an outer collection chamber in one or more relatively well-defined singulated lines exiting from the center cup, thereby improving the consistency of the coating process, while minimizing damage to the biological material potentially caused by collisions between droplets exiting the center cup.

BRIEF DESCRIPTION OF THE DRAWINGS

FIG. 1 is an overall schematic diagram of the method and system of the present invention.

FIG. 2 is a schematic of an electrostatic singularizing apparatus and mixer for use in the present invention.

FIG. 3 is a detailed schematic of the electrostatically singularized droplets formed in the electrostatic mixing process shown in FIG. 2.

FIG. 4 is a representation of an encapsulation apparatus including a spinning disk atomizer.

FIGS. 5A–5D are schematics of a spinning disk atomizer.

FIG. 6 is a detailed cross-section of a preferred embodiment of the conductive charging collar of the electrostatic mixing apparatus.

FIG. 7 is a front view of a preferred embodiment of a stand for the electrostatic mixing apparatus.

FIGS. 8A and 8B are front views of a preferred embodiment of a syringe adapter for use in the preferred embodiment of the spinning disk atomized.

DETAILED DESCRIPTION OF PREFERRED EMBODIMENTS

The present invention provides a system and method for the encapsulation of biological material (e.g., pancreatic islets) that allows for the efficient production of amounts necessary for transplantation. Significantly, with the present invention, biological material encapsulated by a single coating of a polymeric material can be further encapsulated with a second coating with little or no aggregation or clumping together of the capsules. The use of multiple layers ensures substantially complete coverage of the implanted biological material so as to minimize or eliminate the possibility of fibrogenic and/or immune reactions that are destructive to the implant's long-term functionality in the host. Applying additional coatings increases the probability that all parts of the living material are encapsulated. For example, if 5% of the capsules have imperfect coverage with only one coating, a second coating with similar failure rate will reduce the percentage of incomplete encapsulation to 0.25% ($0.05\times0.05=0.0025$).

Referring now to FIG. 1, the overall process of double coating a capsule containing biological material will be described. Unlike conventional double layer coating techniques which include only two steps in which droplets of material are formed (one for forming each coating layer), the present invention incorporates three steps: a first layer coating process as shown generally at 10, an electrostatic mixing process as shown generally at 20, and a second layer coating process as shown generally at 30. While the present invention takes advantage of the combination of all three of these processes 10, 20 and 30, it will be understood that alternative arrangements for accomplishing any of the processes in combination with the other processes as described. For example, any of the known techniques for atomizing and gelling droplets or otherwise creating polymeric material encapsulating viable biological material could be used for either the first coating process 10 and/or the second coating process 30 in connection with the electrostatic mixing process 20. Alternatively, the preferred spinning disk encapsulation apparatus could be used without the electrostatic mixing process to apply one or more polymeric coating layers for coating capsules containing biological material.

A preferred method of the first coating process 10 is an improvement on a first coating process as disclosed in more detail in U.S. Pat. No. 5,578,314 (Cochrum et al.). Typically, the first coating layer is formed by gently combining the biological material 104 into a first polymeric coating composition 102, preferably a suspension of a relatively higher ratio of guluronate relative to mannuronate ("high GIM" alginate). Then, the first polymeric coating composition 102 and biological material 104 are dispersed into droplets using, for example, a spinning cup or disk atomizer 300 to form droplets 120. As described in greater detail below with respect to FIGS. 4 and 5, the spinning disk apparatus of the preferred embodiment is an improvement on the spinning disk apparatus as disclosed in U.S. Pat. No. 5,578,314 (Cochrum et al.). The droplets 120 are collected in a $CaCl_2$ or $BaCl_2$ gelling solution 112, for example, to crosslink or gel the polymer and form single-coated capsules 122. Other potential gelling solutions could include $MgCl_2$ and $ZnCl_2$, or any equivalent divalent cation solution. With pancreatic islets, each capsule 122 may include one or more islets. Preferably, each capsule contains no greater than about 10 pancreatic islets, and more preferably the majority of capsules contain no greater than about 4 pancreatic islets per capsule.

In the preferred embodiment of the process flow as shown at 130 between the first coating process 10 and the electrostatic mixing process 20, the single-coated capsules 122 are then mixed with a $CaCl_2$ solution (preferably, about 2 mM to about 6 mM), removed, mixed with a $CaCl_2$ solution (preferably, about 6 mM to about 12 mM), removed, and finally mixed with a physiologically balanced saline solution in about the same volumetric proportion to the volume of the capsules. The entire process 130 is completed relatively quickly (preferably, between about 10 to 30 minutes). Unlike the techniques disclosed in U.S. Pat. No. 5,578,314 (Cochrum et al.), the process flow 130 uses significantly lower concentrations of the $CaCl_2$ solution and maintains the capsules in the process for a shorter period of time which reduces or eliminates damage to the tissue.

Prior to the present invention, an attempt was made to overcome the prior art problems of aggregation or clumping together of the capsules that occurs in the second coating process by using a dilute suspension of the single-coated capsules in sucrose and dispersing the suspension into a large quantity of a second alginate solution. This resulted in a suspension that could be used in the spinning disk, electrostatic, or air-assist atomizer, or other means for forming droplets without aggregating the capsules and clogging of the apparatus for small quantities of capsules. Unfortunately, it was discovered that using a sucrose solution created a significant biological stress for the encapsulated islets. In addition, the method produced only small quantities of double-coated capsules along with a large number of capsules not containing the single-coated material (i.e., blanks). While it may be possible to select and separate out the blanks after the second coating process is complete, this process can be time consuming and detrimental to the viability of the living tissue. The present invention overcomes many of these problems.

According to the present invention and referring again to FIG. 1, prior to applying the second coating layer, an electrostatic mixing process 20 is used to singulate and separate the single-coated capsule 122. The single-coated capsules 122 in a saline solution used as a liquid carrier medium 200 are mixed with a second polymeric coating composition 214. The liquid carrier medium 200 preferably is a physiologically balanced, low-viscosity solution that has an osmolarity and pH balanced for the particular characteristics of the biological material being encapsulated. In the case of islets, for example, physiologically buffered saline solution. The viscosity of the liquid carrier medium 200 is preferably similar to water. By low viscosity as used in the present invention, it will be understood that the carrier medium 200 has a viscosity of preferably zero or close to zero; however, a viscosity low enough to permit the carrier medium 200 to form the flow stream 204 could also be utilized.

The electrostatic mixing process 20 is preferably accomplished by dispensing the single-coated capsules in carrier medium 200 from syringe 201 mounted in a conductive charging collar 203. Alternatively, the single-coated capsules can be dispensed from a metallic conductive orifice 202 such as a needle, preferably having a diameter of about 0.1 mm to about 2 mm. An electrostatic charge is applied to the conductive collar 203 or conductive orifice 202, preferably at a voltage of about 1 kV to about 100 kV (more preferably, about 5 kV to about 30 kV, and most preferably, about 20 kV). This is described in greater detail below with respect to FIGS. 2 and 3.

The high voltage applied to the conductive charging collar 203 forms an attenuated varicose liquid stream 204 that forms a "varicose bulge" due to the presence of a capsule and breaks up into droplets 210. These droplets 210, which preferably include only one capsule 122 per droplet 210, fall into a second polymeric coating material 214, preferably an alginate with a relatively higher ratio of mannuronate relative to guluronate ("high M/G" alginate) as disclosed in U.S. Pat. No. 5,578,314 (Cochrum et al.). The second polymeric coating composition 214 is preferably at ground potential as shown at 216. The high voltage, which is applied by a charging collar 203, serves to force the liquid from the syringe 201 into a conical shape, which then forms a ligament structure punctuated by bulges or a varicose structure formed by the capsules 122. The thinning of the liquid stream 204 serves to separate the capsules 122 into an approximate linear sequence. The bulges produce a radius of curvature in the streamwise direction, which causes the liquid to collapse in the streamwise or longitudinal direction under the force of surface tension into either a thin layer of saline solution around the individual capsules 122 before they are driven into the second polymeric coating composition 214 by the electrostatic forces or into a sphere of saline solution. Although ideally this results in singularized capsules (i.e., only one single-coated capsule per droplet), there may be droplets 210 that include more than one capsule 122. Preferably, at least ninety percent (90%) of the droplets 210 contains no greater than about 4 capsules per droplet. More preferably, a majority of the droplets contains no greater than about 2 capsules per droplet.

Preferably, the droplets 210, which contain a saline carrier 200 and single-coated capsules 122, are introduced in the second polymeric coating material 214 with mixing, typically caused by a vortex mixer 213 to assist the single-coated capsules 122 from aggregating in the solution 214. While a vortex mixer 213 is preferred, it will be recognized that other forms of mixing such as vibratory, shaking or ultrasonic could also be utilized to agitate the second polymeric coating material 214. Less preferably, a mechanical mixing arrangement such as a stirring or folding arrangement could be used, although the mechanical operation of a mixing apparatus within the second polymeric coating material 214 may tend to increase the potential for damage to the biological material in the capsules. Together with the electrostatic separation charge supplied to the capsules 122 by the charging collar, a uniformly dispersed suspension 222 of single-coated biological material in the second coating material 214 is provided.

The second coating material 214 containing the separated capsules 122 is transferred at process step 230 into the second coating process 30. The electrostatic mixing process of the invention allows for separated capsules 122 to be present in coating material 214 at concentrations much higher than was previously possible. Since the concentration of separated capsules 122 is so high, less coating material 214 is required and, the number of blanks generated during second coating process 30 is greatly reduced. Using conventional techniques, in the most favorable cases the second coating process would produce blanks at a ratio of at least 10:1 to encapsulated cells, and more commonly at a blank ratio of 50:1. In contrast, the preferred embodiment of the present invention produces blanks during the second coating process at a ratio of less than 10:1 and more typically at a blank ratio of 6:1 or better.

In the second coating process 30, the second polymeric coating composition 214 containing the single-coated capsules 122 is formed into droplets 320 using a spinning disk atomizer 300 or other mechanical or electrostatic dispensing means that are subsequently gelled to form double coated capsules 322 containing the previously single-layer encapsulated living biological material. Preferably, the encapsulation apparatus 300 includes a spinning disk atomizer 302 that is used in the second encapsulation process 30. The atomizer 302 receives single-coated capsules 122 suspended in the second polymeric coating composition 214 from a syringe 304 and catheter 306. This syringe 304 and catheter 306 are positioned above the spinning disk atomizer 302. The tip of the catheter 306 is typically placed very close to the bottom of a reservoir 504 in a spinning center cup 502 of the spinning disk atomizer 302.

Preferably, an automated motion control apparatus is used to adjust the tip of the catheter 306 relative to the bottom of the reservoir 504. In this embodiment a conductive replica of the catheter tip 306 is inserted on the syringe 304 to measure when the catheter tip 306 would be at the bottom of the reservoir 504 by sensing electrical conductivity between the conductive replica of the catheter tip 306 and the center cup 502. An automated motion control system with a corresponding position sensor/detector then selectively steps the syringe adapter 340 holding the syringe 304 such that the catheter tip 306 is stepped away from the bottom of the reservoir 504 a predetermined distance. Preferably, this distance is greater than about 500–600 microns or the largest diameter of the capsules to be created), but less than about 1500 microns. The optimum standoff distance of the catheter tip 306 from the bottom of the reservoir 504 in this range can be determined without undue experimentation by a person skilled in the art dependent upon the particular characteristics of the capsules, biological material, rotational speed(s) of the spinning disk atomizer 302 and qualities of the polymeric coatings.

A drive mechanism 308 is preferably used to feed the mixture at a fixed flow rate. The spinning disk atomizer 302 is then rotated at an appropriate speed. Through centrifugal motion, spherical droplets 320 of the suspension material 222 of about 50 microns to about 500 microns in diameter are produced. The suspension material 222 rises up the walls of the center spinning cup 502 of the spinning disk atomizer 302 by centrifugal force and forms an outward radial flow of the suspension material 214, preferably under directional impetus from grooves in the wall of the spinning cup 502 as will be described. The droplets 320 are then collected in an outer collection chamber 310, preferably, an annular collection dish. The outer collection chamber 310 is filled with a gelling solution 312 as described in U.S. Pat. No. 5,578,314 (Cochrum et al.), for example. Typically, the gelling solution 312 is a calcium chloride or barium chloride solution. Other potential gelling solutions could include $MgCl_2$ and $ZnCl_2$, or any equivalent divalent cation solution.

After the second coating step 30, the suspension with the encapsulated islets is then collected and placed into sterile containers (e.g., 50-ml conical tubes) to settle. After the double-coated capsules 322 have settled, approximately two thirds of the gelling solution 312 is removed. The double-coated capsules 322 are then combined into a single tube and allowed to settle again. This process typically does not require more than about 10 minutes. The remainder of the gelling solution is carefully removed, replaced with a lesser concentration of buffered calcium chloride solution (preferably, between 1–5 mM) and allowed to settle for about 10–30 minutes. After this, the calcium chloride solution is removed, cell culture media is added to the double coated capsules, and this mixture is plated out and put into an incubator.

An advantage of the present invention is that the multilayer coating is applied in a short time so that the living biological material is not stressed and a high degree of viability is maintained. In a preferred embodiment, the total processing time for batches of at least 100,000 cell clusters is less than two to three hours. Also, the present invention allows for the coating of relatively large-scale batches of at least 100,000 cell clusters per batch and optimally more than 500,000 cell clusters per batch. Furthermore, effective singularizing of the single-coated capsules allows for the application of a second polymeric layer of a substantially uniform thickness to a large number of the individual capsules in a convenient, controllable, and reproducible manner. Multilayered capsules containing islets produced with this approach have been shown to function normally for more than one year in mice.

Thus, significantly, the present invention reduces the amount of aggregation of the single-coated capsules during the second coating process and allows the subsequent coatings to be applied to a high percentage of the capsules and allows for good bonding between coating layers. The thickness and permeability of the coatings may be controlled by the selection of the various process parameters. The concentration of the capsules in the alginate suspensions can be maintained at a higher density without aggregating or gelling. Most importantly, all of this is accomplished in such a way as to provide for the consistent and effective manufacture of large-scale batches of cell clusters. The fact that the present invention can process large-scale batches of cell clusters allows for double layer encapsulation of all of the cell clusters from a donor organ as part of one large-scale batch process. The ability to process an entire donor organ in a single process is desirable from a number of perspectives, including quality control, efficiency and regulatory approval.

The following sections provide more details about each of the portions of the process and apparatus of the present invention. In the following description, the process is described in terms of encapsulating pancreatic islets; however, it can be applied to a variety of biological materials as will be understood by one of skill in the art. Such biological materials include living tissues, cells, cell lines, and other biologically active substances intended to be implanted into the body of a host. Examples include, but are not limited to, pancreatic islets, hepatic cells, neural cells, renal cortex cells, vascular endothelial cells, thyroid cells, adrenal cells, thymic cells, and ovarian cells. Preferably, the biological material includes pancreatic islets. For purposes of the present invention, the biological material to be encapsulated will be generally referred to as cell clusters, recognizing that such a cell cluster may contain as little as one cell or a very large number of cells, but preferably such cell clusters are arranged to yield a double coated capsule having an average final resulting diameter on the order of no more than about 350–600 microns.

Preferred Initial Encapsulation Process

Islets from a donor are typically maintained in sterile cell culture dishes. These islets are collected, allowed to settle, washed, and placed in a saline solution. This can be done by placing them in conical tubes (e.g., of about 50-ml volume), for example. Cell culture media is carefully removed, for example using a pipette. The collected cells are combined into one tube and allowed to settle and are then washed with a suitable buffer. For example, a solution containing 0.9 wt-% sodium chloride buffered with 10 mM HEPES (N-[2-hydroxyethyl]piperazine-N'-[2-ethanesulfonic acid]) (pH 7.2) can be used. The islets are again allowed to settle in the conical tube and the washing process is repeated, typically three times (with about 30 milliliters (ml) for each washing). The islets are then transferred to a shorter conical tube after the third wash and excess saline solution is removed until the volume of saline is approximately equal to twice that of the islets. The saline drawn off in this manner is discarded.

The islets are coated with a first polymeric coating. This can be done using a variety of suitable polymeric materials. Such coating materials are preferably sufficiently permeable to permit effective diffusion of nutrients and other essential biological materials into the transplanted material and passage of transplant tissue products therefrom into the host system. Typically and preferably, the polymeric coating materials for the first coating are water-soluble, natural or synthetic polysaccharides, typically in the form of gums. Examples include, but are not limited to, alginates, guar gum, gum arabic, charageenan, chitosan, pectin, tragacanth gum, xanthan gum, or acids thereof. Preferably, the first coating material is an alginate containing a relatively high level of guluronate relative to mannuronate ("high G/M" alginate or simply "G alginate" coating composition), preferably wherein the mannuronate alginate to guluronate alginate is in a ratio of greater than about 50:50 as disclosed in U.S. Pat. No. 5,578,314 (Cochrum et al.). More preferably, the polymer composition is prepared according to Example 1 of U.S. Pat. No. 5,578,314 (Cochrum et al.).

The islets can be coated with such polymeric materials in a variety of ways. In one embodiment, the saline and islets are drawn up with a syringe of appropriate volume with an appropriate size catheter (e.g., 14-gauge catheter), for example, to collect all of the saline plus islets. The suspension is drawn completely into the syringe taking care not to introduce air bubbles. The G alginate (preferably, diluted to about 1.5%) is placed into a second syringe of appropriate size, which is then attached to one side of a Y-syringe connector which has been primed with alginate. The syringes containing the islets and saline are attached to the other side of the Y-connector. The islets in saline and the alginate are mixed by emptying their respective syringes simultaneously through the Y-connector into a container (e.g., a settling tube). The mixing of the alginate and islets in the container is continued by any suitable mechanical agitator (e.g., a vortex mixer), taking care not to introduce air bubbles, until a uniform mixture has been achieved.

In a preferred embodiment, the islets are transferred to a syringe 100 with an equal volume of saline. An amount of G-alginate with a weight approximately equal to the weight of the islets and saline is placed in a container (not shown) and the syringe 100 is used to draw the G-alginate into the islets. Gently mixing of the G-alginate with the islets can be accomplished by any of a variety of techniques. Preferably, the G-alginate and islets are gently mixed by manually rolling or otherwise manipulating the syringe 100 to obtain a uniform mix and color of the first alginate suspension. The relative volumes of the islets plus saline and the first polymeric coating composition are selected to produce a mixture having a sufficient viscosity for adequate mixing and coating and to provide the desired thickness and morphology of the coating. Preferably, for a 1% alginate solution, the viscosity is about 15 centipoise (cps) to about 5000 cps. A preferred range of solution for the first alginate solution is between 1% and 2%. These relative amounts can be determined without undue experimentation by one of skill in the art. It will be recognized that other forms of dispersing the cell clusters with the first polymeric coating solution can also be used, such as mechanical dispersion or liquid dispersion.

Figure 4:
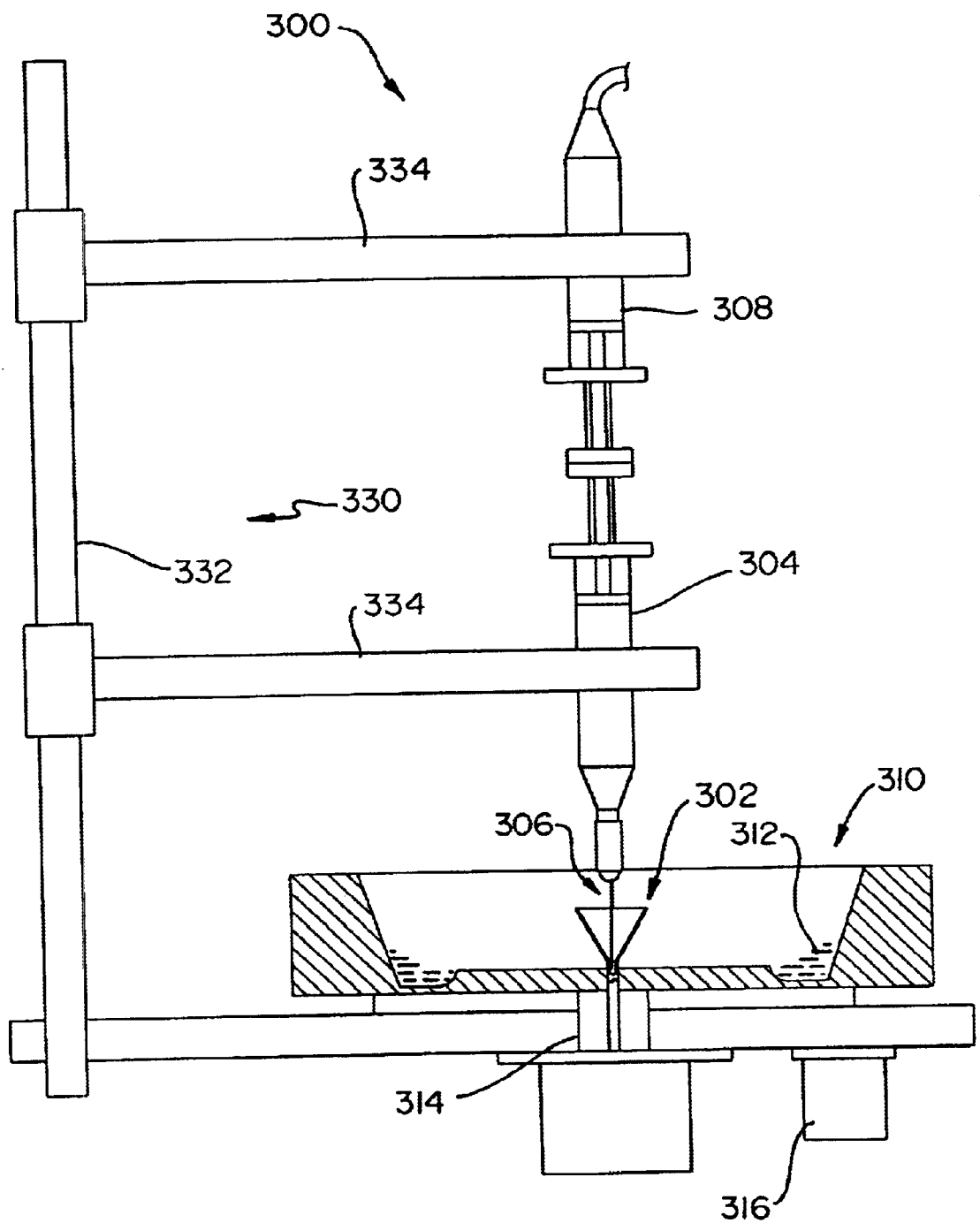
Figure 5A:
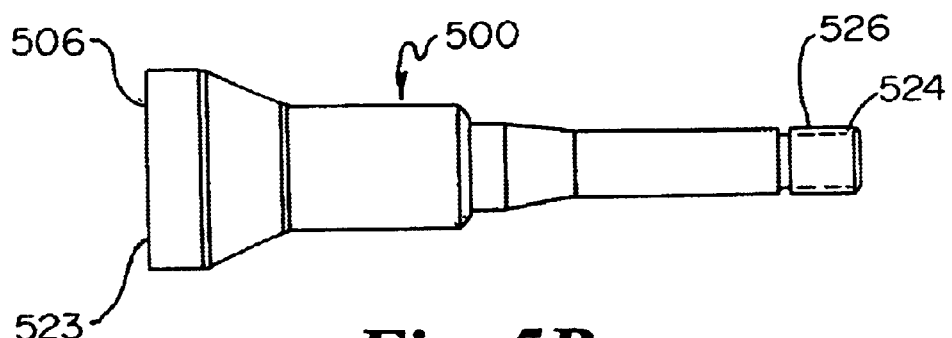
Figure 5B:
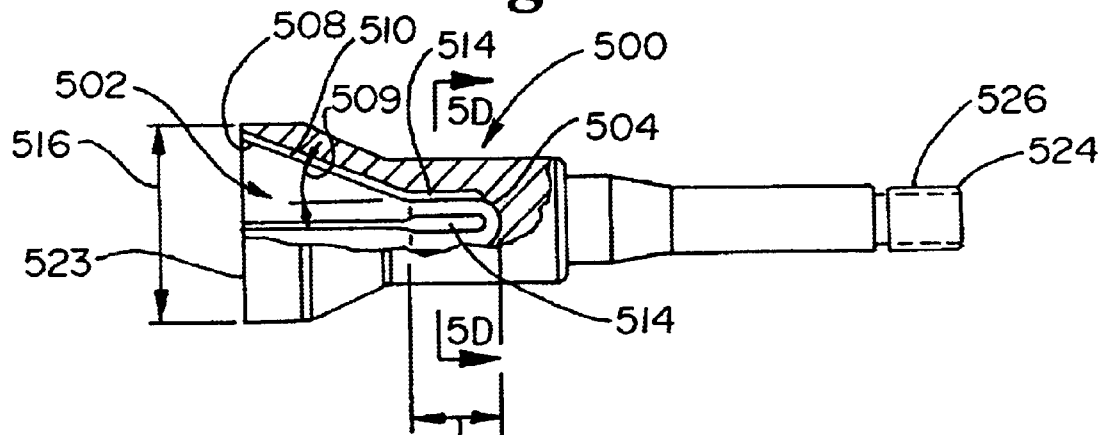
Figure 5C:
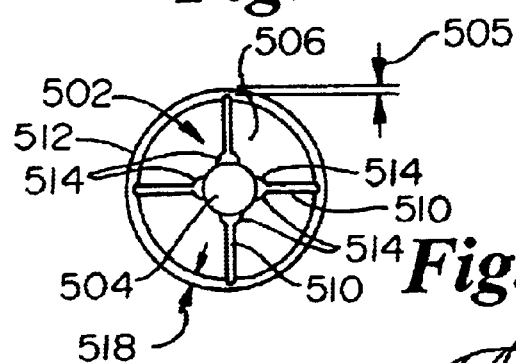
Figure 5D:
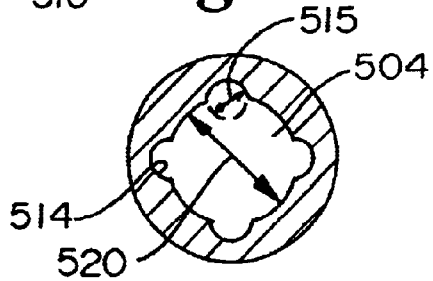

The process of coating includes a variety of techniques to atomize and gel this first coating composition. For example, the methods described in U.S. Pat. No. 5,578,314 (Cochrum et al.) and U.S. Pat. No. 5,643,594 (Dorian et al.) can be used if desired to prepare capsules containing islets with a first polymeric coating thereon. Alternatively, any of the other known techniques previously discussed for atomization and droplet formation, as well as for gelling and coating the capsules. Preferably, a spinning cup or disk atomizer 300 as described below in connection with FIGS. 4 and 5 is used to form droplets. The droplets are typically collected in a $CaCl_2$ or $BaCl_2$ gelling solution, for example, to crosslink or gel the polymer and form single-coated capsules.

Electrostatic Mixing Process

The single-coated living biological material is encapsulated with a second polymeric coating. This can be done using a variety of suitable polymeric materials. As with the first coating material, these coating materials are preferably sufficiently permeable to permit effective diffusion of nutrients and other essential biological materials into the transplanted material and passage of transplant tissue products therefrom into the host system. Typically and preferably, the polymeric coating materials for the second coating are water-soluble, natural or synthetic polysaccharides, typically in the form of gums. Examples include, but are not limited to, alginates, guar gum, gum arabic, charageenan, chitosan, pectin, tragacanth gum, xanthan gum, or acids thereof. Preferably, the second coating material is an alginate containing a relatively high level of mannuronate alginate relative to guluronate alginate ("high M/G alginate" or simply "M alginate" coating composition), preferably wherein the guluronate alginate to mannuronate alginate is in a ratio of greater than about 50:50 as disclosed in U.S. Pat. No. 5,578,314 (Cochrum et al.).

Prior to application of the second coating, the single-coated capsules are collected and washed with a suitable agent, typically three times (with about 30 ml for each washing). For example, a solution containing 0.9 wt-% sodium chloride and 3 mM calcium chloride (pH 7.2) buffered with 10 mM HEPES can be used. The single-coated capsules are then mixed with a suitable carrier for introduction into the second polymeric coating composition. For example, the carrier can include 0.9 wt-% sodium chloride buffered with 10 mM HEPES.

Figure 2:
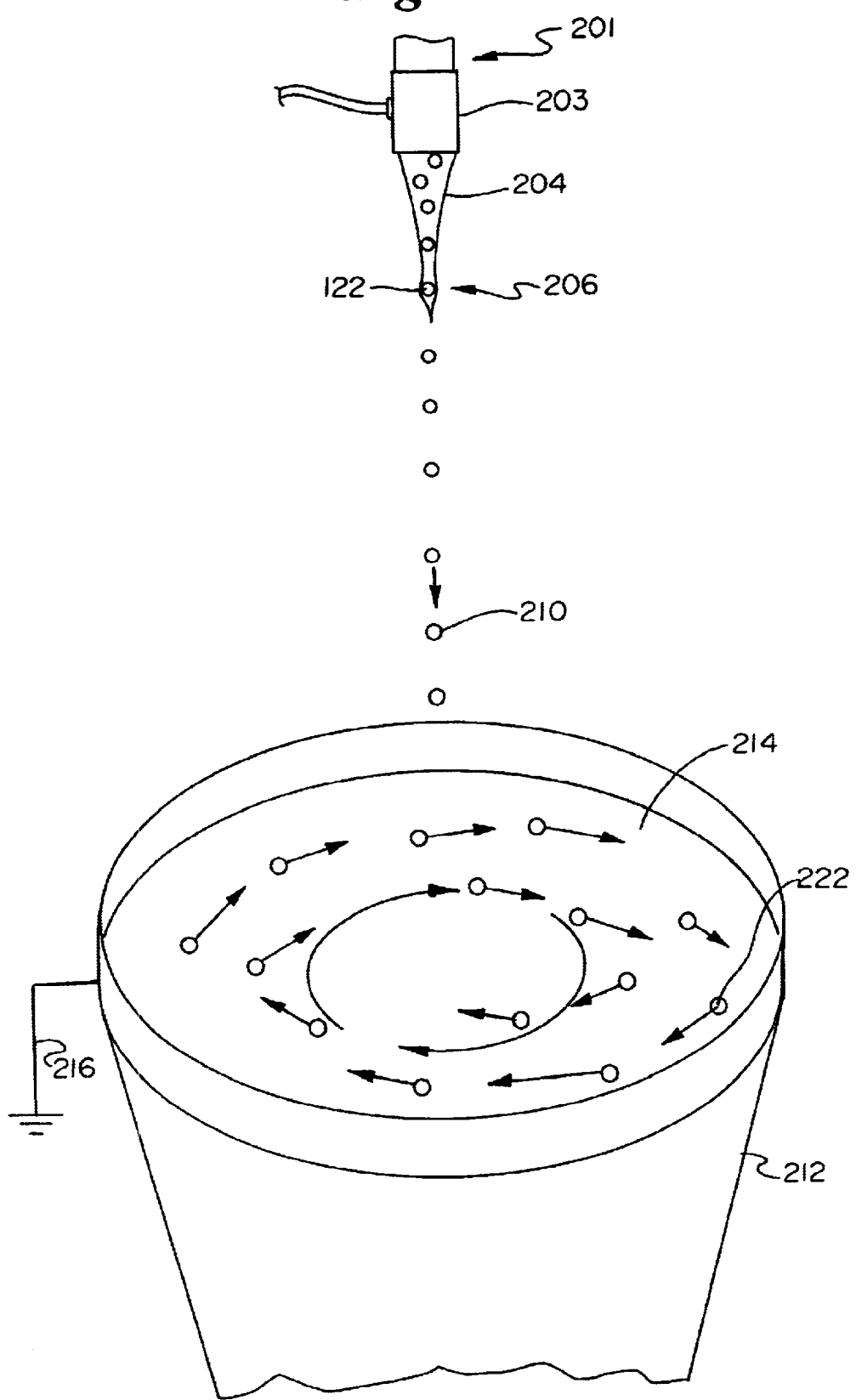
Figure 6:
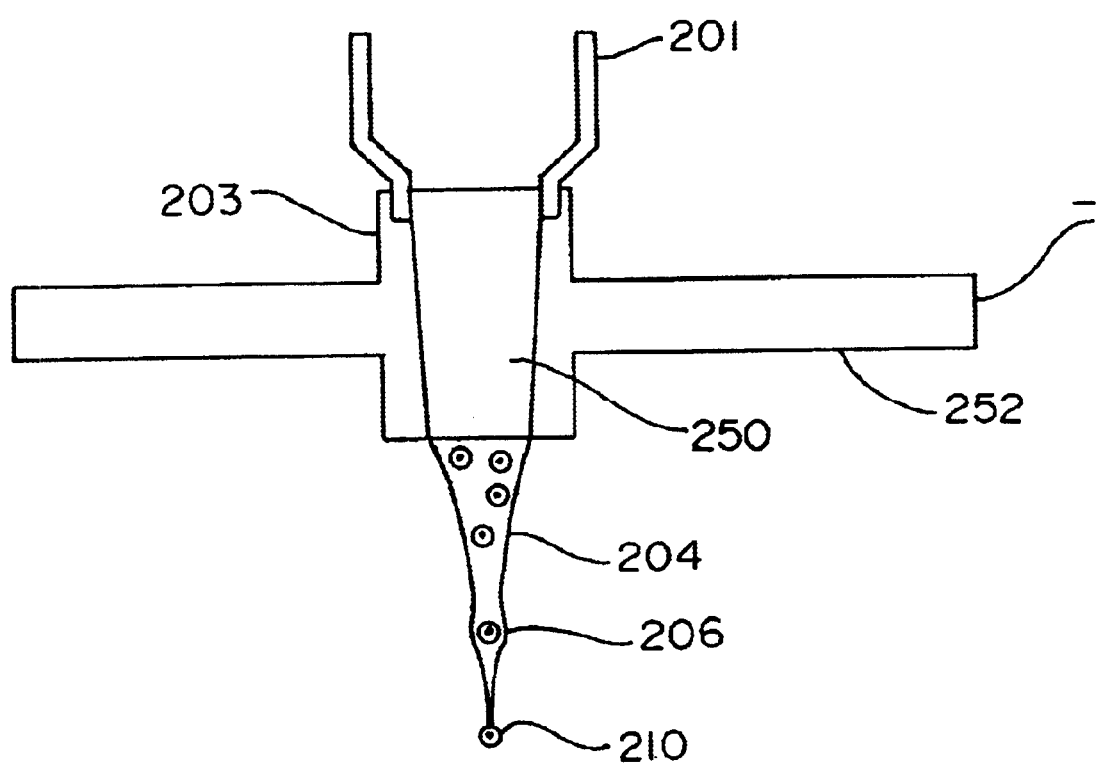

In one embodiment of the electrostatic mixing process, as shown in FIG. 2, the suspension of single-coated capsules in a carrier (e.g., physiological saline) is placed in a syringe 201 or other suitable means. The mixture is gently agitated to ensure that the mixture is uniform. Any entrained air bubbles are preferably allowed to float to the top surface. The syringe containing the single-coated capsules preferably has a conductive orifice as a result of the tip of syringe 201 being mounted within a stainless steel charging collar 203 or fitted with a conductive orifice 202 or other conductive material. The orifice 202 preferably has a diameter of about 0.2 mm to about 5 mm, and more preferably about 1.5 mm to about 2 mm. As shown best in FIG. 6, the charging collar 203 is located about a syringe 201 for purposes of applying the electrostatic separation charge. Preferably, the conductive charging collar 203 includes a slightly tapered center channel 250 through which the carrier medium 200 containing the single-coated capsules is forced. Preferably, the orifice 202 or charging collar 203 is connected to a high voltage source to provide a DC voltage of about 1 kilovolt (kV) to about 100 kV (more preferably, about 5 kV to about 30 kV). In a particularly preferred embodiment, the electrostatic voltage is set at approximately 20 kV.

Figure 7:
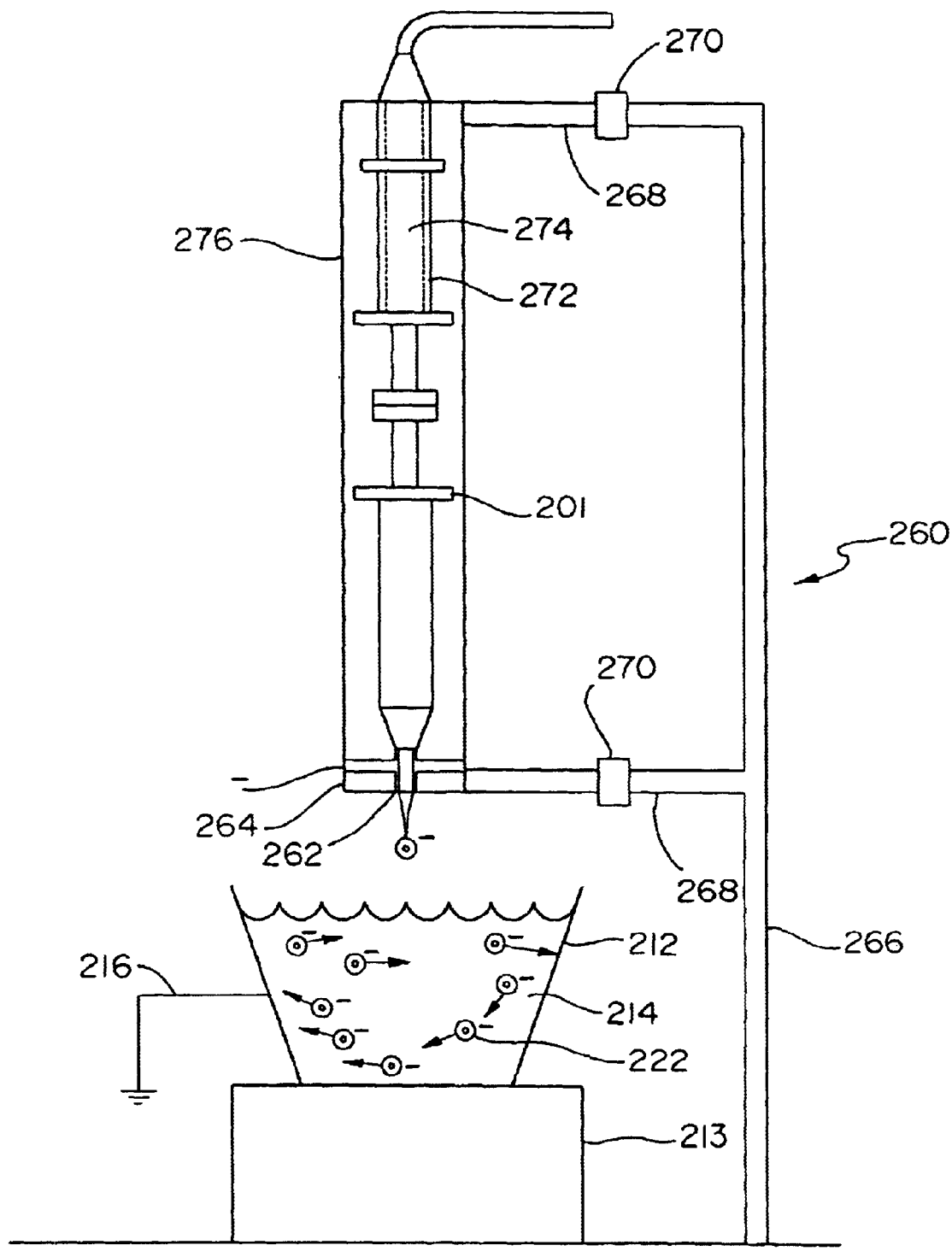

In a preferred embodiment as shown in FIG. 7, the charging collar 203 includes a flange portion 252 about the center of the charging collar 203 that is supports the charging collar 203 with the syringe 201 mounted therein in a slot 262 of a base 264 of a stand apparatus 260. Preferably, a stabilized mounting column 266 of the stand apparatus 260 is electrically isolated from at least a pair of mounting arms 268 by a corresponding pair of insulators 270. A syringe driver 272 is slidably mounted on a channel 274 defined in a face bracket 276 that is connected between base 264 and a top one of the mounting arms 268. The syringe driver 272 may be selectively moved and locked in a desired position by a wing nut or equivalent releasably locking mechanical arrangement. The syringe driver 272 is preferably fluidly coupled to an automated pumping apparatus (not shown) that precisely controls an amount of fluid driven into the syringe driver 272. Alternatively, a stepper motor or other automated motion control apparatus could be used to drive the syringe 201 to expel the first polymeric suspension 200.

In this electrostatic mixing process, the syringe driver 272 is used to force the suspension at a preselected constant flow rate through the orifice 202 or charging collar 203. The charge induced in the liquid forces the liquid out the orifice and into a sinuous threadlike fiber or ligament. The process of drawing out the liquid into the conical shape is shown schematically in FIG. 3. The high voltage on the collar is adjusted to produce a single sinuous stream of liquid, given a preset flow rate. For a particularly preferred embodiment, the voltage and flow rate are set at 20 kV and 2.75 ml/min in a preferred embodiment, and an approximate current of 0.1 mA (milliampere). It will be seen that both the flow voltage and flow rate associated with the electrostatic mixing process 20 of the preferred embodiment of the present invention are significantly different than flow rates (typically less than 0.5 ml/min) used in conventional electrostatic droplet generators for polymeric coating materials having similar properties to the properties of the coating materials described herein.

Figure 3:
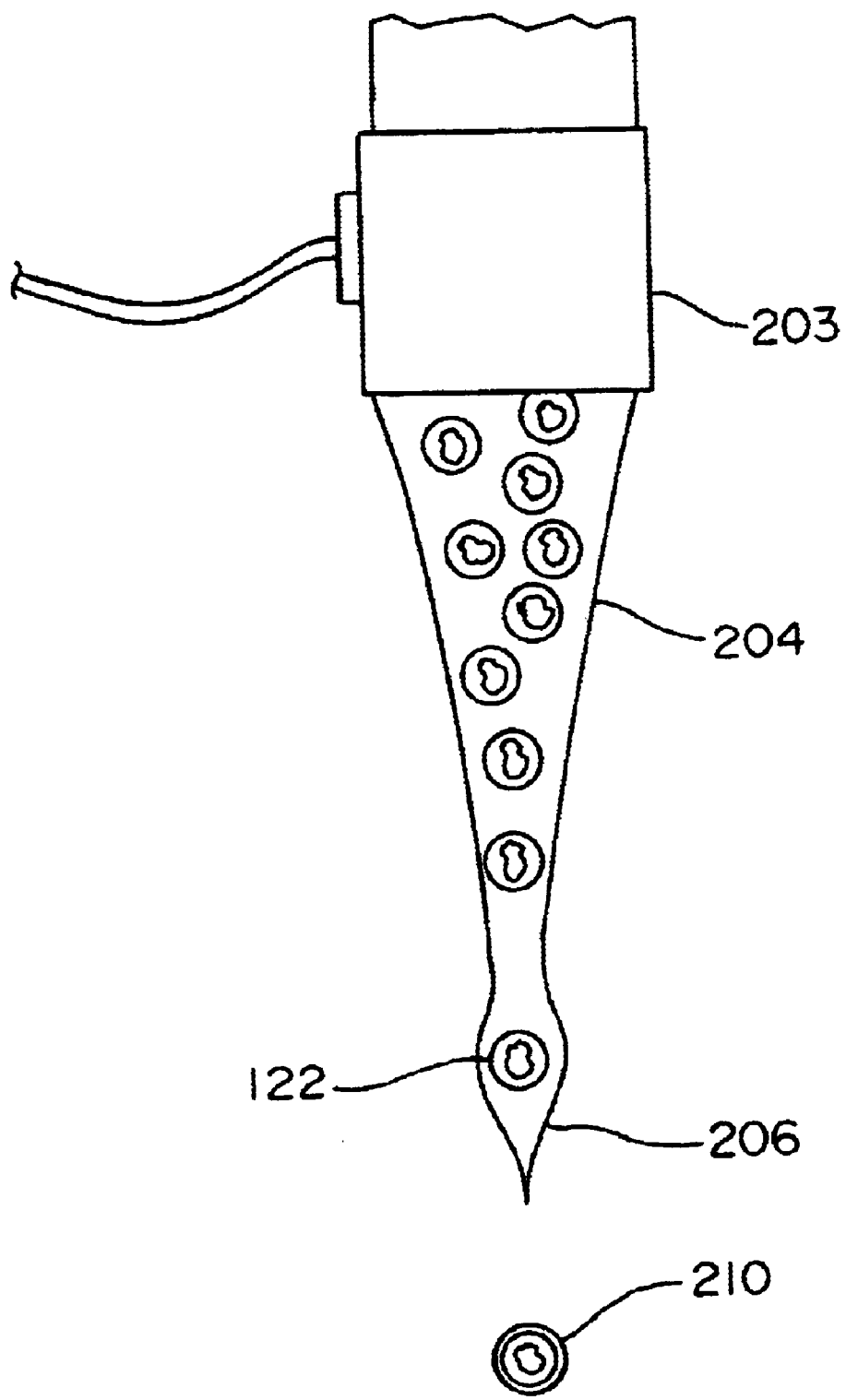

Referring to FIG. 2, and as shown in greater detail in FIG. 3, the high voltage applied to the conductive orifice 202 or charging collar 203 forms an attenuated varicose liquid stream 204 that forms a "varicose bulge" 206 due to the presence of a capsule 122 and breaks up into droplets 210. These droplets 210, which preferably include only one capsule 122 fall into a second polymeric coating material 214.

The second polymeric coating composition, preferably at ground potential, in a container 212 of a vortex mixer 213 is located beneath the electrostatic discharge orifice to collect the droplets 210. The vertical distance from the top of the container 212, or the surface of the second coating composition 214 contained therein, to the exit of the syringe 201 is adjusted to produce an adequate electrostatic field, and to allow complete separation of the droplets 210 as they fall from the syringe. This distance can be experimentally determined without undue experimentation by one of skill in the art. It can range from millimeters to meters.

As shown in FIG. 2, the droplets 210 impact the moving surface of the second polymeric coating composition 214 and are swept into the composition through the agitation action of the mixer 213. The high relative potential on the capsules 122 in the droplets 210 provides the additional force needed to drive the capsules into the viscous polymeric composition. Since liquid alginate is semi-conductive, a residual charge will likely remain in the single-coated capsules ("G" alginate) even after they are engulfed by the high mannuronate alginate ("M" alginate). This residual charge is believed to serve to help prevent aggregation of the capsules. Thus, the mixing step 20 of this invention facilitates singularizing the capsules and then separating the capsules to disperse them effectively into the second polymeric coating composition, thereby forming a "suspension" or "suspension material."

The relative volumes of the single-coated islets plus carrier and the second polymeric coating composition are selected to produce a mixture having a sufficient viscosity for adequate mixing and coating and to provide the desired thickness and morphology of the coating. Unlike the prior art techniques that required larger amounts of the second polymeric coating, the electrostatic mixing process 20 of the present invention requires much smaller quantities of the second polymeric coating solution 214. For a given volume of single-coated capsules 122 in saline solution 200 (e.g., a volume of capsules 122 in approximately one to two times, and preferably about 1.5 times, the same volume of saline solution 200, the weight of second alginate solution 214 required for effective encapsulation is between about two to three times the combined weight of the capsule 122 and saline 200, and more preferably about 2.2 times the combined weight of the capsules 122 and saline 200. The amounts and volumes of the second alginate solution 214 are preferably chosen to yield a range of about 2.5% to 4% of the M-alginate, and more preferably about 2.8%.

The mixer 213 is allowed to run for a sufficient amount of time (e.g., at least approximately 30 seconds) to ensure that complete mixing of the capsules, saline, and the second polymeric coating composition takes place. Preferably, the mixer 213 is bolted or otherwise secured to a workbench to insure more uniform agitation action. With other encapsulation polymers and biological material, the time may be longer or shorter. This could be determined experimentally. One skilled in the art would easily determine what level of mixing is appropriate for the process at hand. Failure to completely mix the suspension may not result in a homogeneous suspension, which can be detrimental to the second coating process.

Preferred Encapsulation Process

Once the single-coated islets are mixed with the second polymeric coating composition, the single-coated islets are encapsulated with a second coating. FIG. 4 illustrates an encapsulation apparatus 300 including a spinning disk atomizer 302 that is preferably used in the second encapsulation process. The atomizer 302 receives single-coated islets suspended in the second polymeric coating composition (referred to collectively as the "suspension material" or "suspension" from the previous electrostatic mixing process), from a syringe 304 and catheter 306 (e.g., 20-gauge catheter). This syringe 304 and catheter 306 are positioned above the spinning disk atomizer 302. The tip of the catheter 306 is typically placed very close to the bottom of the reservoir of the spinning disk atomizer 302 (typically, about 0.7 mm from the bottom of the spinning disk reservoir) as shown in FIG. 4. A drive mechanism 308 (e.g., a syringe pump) is preferably used to feed the mixture at a fixed flow rate (e.g., between 0.5 ml/minute and 5 ml/minute and preferably about 1.2 ml/minute for the particular configuration of the size and shape of the atomizer 302 of the preferred embodiment).

Once the single-coated capsules in the second suspension 222 have just filled the bottom of a reservoir portion (as described below with reference to FIG. 5), the spinning disk atomizer 302 is then rotated at an appropriate speed. Through centrifugal motion, spherical droplets of the suspension material of about 50 microns to about 500 microns in diameter are produced. This is referred to herein as atomization. The suspension material rises up the walls of the spinning disk atomizer by centrifugal force and forms an outward radial flow of the suspension material from grooves in the wall (described in greater detail below). The droplets 320 are then collected in an outer collection chamber 310, preferably, an annular collection dish. The collection dish is preferably formed of a polypropelene material, although other plastic or metal materials could be used. The outer collection chamber 310 is filled with a gelling solution 312 as described in U.S. Pat. No. 5,578,314 (Cochrum et al.), for example. Typically, the gelling solution 312 is a calcium chloride solution. Preferably, this includes about 150 ml of 10 mM HEPES buffer with 120 mM calcium chloride solution (pH 7.2).

The spinning disk atomizer 302 is rotated until the syringe 304 is empty. The outer annular collection chamber 310 is also rotated at a speed sufficient to attain a sufficient depth of the gelling solution in the inside of the outer wall. The direction of rotation of the annular collection chamber 310 is preferably the same direction as the direction of rotation of the spinning disk atomizer 302. Preferably, a wall of the outer collection chamber 310 is slightly angled at an angle equivalent to an angle of the gelling solution 312 tends to maintain when the outer collection chamber 310 is rotated at the desired operating speed.

The spinning disk atomizer 302 may be operated at different rotational speeds depending on the size of drops required and the diameter of the center reservoir, the viscosity and surface tension of the polymeric composition, and other process parameters. One skilled in the art would know that the fundamental correlations for rotating atomizers and/or experimental trials could be used to establish the desired operating conditions. Also, one skilled in the art would recognize that the tangential component of the drop velocity of the droplet should be similar to the tangential speed of the outer collection chamber 310.

Preferably, the spinning disk atomizer 302 is rotated at a rate of about 2000 revolutions per minute (rpm) to about 8000 rpm, and more preferably, at a rate of about 4000 rpm. Preferably, the outer collection chamber 310 is rotated at a speed of between 300 to 500 rpm. In a preferred embodiment, the distance between the edge of the atomizer 302 and the outer collection chamber is between 5–20 cm, although the optimum distance will depend upon the speeds at which both the spinning disk atomizer 302 and the outer collection chamber 310 are rotated.

The suspension with the encapsulated islets 322 is then collected and placed into sterile containers (e.g., 50-ml conical tubes) to settle. After the double-coated capsules have settled, approximately two thirds of the gelling solution is removed. The double-coated capsules are then combined into a single tube and allowed to settle again. This process typically does not require more than about 10 minutes. The remainder of the gelling solution is carefully removed, replaced with 30 ml of 10 mM HEPES buffer mixed with 0.9 wt-% sodium chloride and 3 mM calcium chloride solution (pH 7.2), and allowed to settle for about 30 minutes.

As shown in FIG. 4 and FIGS. 8a and 8b, a preferred embodiment of the encapsulation apparatus 300 utilizes an adjustable syringe adapter 340 to accommodate different size syringes 100, 304 in a stand apparatus 330. The stand apparatus 330 includes a support column 332 and a pair of support arms 334 that are preferably selectively shiftable on the support column to accommodate different sizes of syringes 100, 304. The adapter 340 is preferably seated in an aperture (not shown) defined on a lower one of the support arms 334, although other mechanical arrangements for mounting the adapter 340 to the support arm 334 are contemplated. The adapter 340 includes an upper portion 342 with a tab 344 and a bottom portion 346 with a tab 348 each having a corresponding aperture 350, 452 for accommodating a syringe of a particular size. The distance between the upper tab 344 and the bottom tab 348 is preferably selectable, such as by including an upper channel 354 and a bottom channel 356 with a mating extension bar 358 releasably secured to each portion 342, 346 of the adapter 340. Any of a number of alternative mechanical arrangements for selectively positioning the height of the upper tab 344 relative to the bottom tab 348 could also be utilized. In one embodiment for islet cells as shown in FIGS. 8a and 8b, an adapter 340 is provided for each of a number of different size syringes, such as a 3 ml (for up to about 100,000 cell clusters), 12 ml (for up to about 350,000 cell clusters), 35 ml (for up to about 750,000 cell clusters) and 60 ml (for up to about 1,200,000 cell clusters.

Spinning Disk Atomizer

Attention is now directed to the particular construction of an exemplary spinning disk atomizer 500 as illustrated in FIGS. 5A–5D. A more expanded description of an exemplary spinning disk atomizer of this type without the uniquely modified central spinning cup of the present invention is shown and described in U.S. Pat. No. 5,643,594 (Dorain et al.) and U.S. Pat. No. 6,001,387 (Cochrum), the disclosures of which are hereby incorporated by reference. While described with particularity, the atomizer illustrated in the accompanying figures and discussed below is intended to be exemplary only. Modifications to the spinning disk atomizer 500 as well as to the remainder of the encapsulation apparatus are certainly possible without departing from the scope of the invention. It is preferred that the spinning disk atomizer 500 is used for both the first coating process 10 and the second coating process 30, although it will be understood that other atomization and gelling techniques could be used for one or the other of these coating processes with lesser effectiveness.

Referring again to FIG. 4, during operation, the atomizer 302 is filled via the catheter 306 with the suspension material until the level reaches the top (i.e., the point at which the grooves meet the reservoir) of the reservoir (504, FIG. 5B). The drive motor 314 is then activated and the atomizer 302 begins to rotate. While the rotational speed of the atomizer 302 may vary depending on factors such as atomizer size and configuration, suspension material viscosity, etc., speeds in the range of about 2000 rpm to about 8000 rpm have been found to produce satisfactory results. As the atomizer 302 spins, friction between the atomizer and the suspension material accelerates the latter, causing it to rise up out of the reservoir portion (504, FIG. 5B) and onto the frustoconical wall portion (508, FIG. 5B). The wall portions and the grooves (508 and 522, 510 and 514, FIG. 5B) assist the flow of the suspension material upwardly and outwardly. When the suspension material reaches the lip (512, FIG. 5C), ligaments or spherical drops form and are projected radially outward.

Due to centrifugal forces, the ligaments are dynamically unstable. Surface tension ultimately causes the ligaments to format spherical drops of nearly uniform size. These drops preferably have a diameter that ranges from about 100 μm to about 350 μm. The actual diameter is dependent on many factors though, including rotational speed, flow rate to the atomizer, surface tension and viscosity of the suspension material, and the size of the biological material encapsulated to name a few.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A system for encapsulating cell clusters of biological material comprising:

means for atomizing and gelling a first alginate suspension containing cell clusters of the biological material in a first alginate solution to form capsules having a first layer coating surrounding at least a portion of the cell clusters;

means for applying an electrostatic charge to a liquid carrier medium containing the capsules prior to introducing the carrier medium into a second alginate solution to create a second alginate suspension; and means for atomizing and gelling the second alginate suspension containing the capsules to form a second layer coating around the capsules.

2. The system of claim 11, wherein the means for atomizing and gelling the second alginate suspension comprises a spinning disk encapsulation apparatus having a center cup into which the second alginate suspension is introduced and an outer collection chamber containing a gelling solution.

3. The system of claim 2, wherein the center cup includes an opening, a reservoir and an inner wall defined between the opening and the reservoir with at least one groove defined on the inner wall.

4. The system of claim 3, wherein the inner wall comprises at least a frustoconical surface tapered outward and having a plurality of grooves defined on the surface.

5. The system of claim 4, wherein the plurality of grooves include a first set of grooves defined on the frustoconical surface and a second set of grooves defined on a second wall surface above a top of the reservoir and below the frustoconical surface, at least a portion of the first set of grooves aligned with the second set of grooves.

6. The system of claim 4, wherein the plurality of grooves are evenly spaced about the surface.

7. The system of claim 2, wherein the center cup of the spinning disk encapsulation apparatus is operated at a speed of between 2000 rpm and 8000 rpm.

8. The system of claim 1, wherein the means for atomizing and gelling the first alginate suspension and the means for atomizing and gelling the second alginate suspension comprise the same apparatus.

9. The system of claim 1, wherein the means for applying an electrostatic separation charge is operated at a voltage of between 1 kV to 100 kV.

10. The system of claim 1, further comprising:
means for mechanically agitating the second alginate solution as the carrier medium containing the capsules is introduced into the second alginate solution.

11. A method for encapsulating biological material, the method comprising:
providing a composition comprising a liquid carrier and polymeric capsules, wherein the polymeric capsules comprise biological material in a first polymeric coating and the carrier comprises a low viscosity solution;
applying an electrostatic charge to the composition prior to generating a flowing stream of droplets of the composition, wherein at least a portion of the droplets comprise biological material;
introducing the flowing stream of droplets into a second polymeric coating composition to form a suspension; and
atomizing and gelling the suspension to create a second polymeric coating.

12. The method of claim 11, wherein the biological material comprises pancreatic islets and wherein at least a majority of the polymeric capsules each include at least one islet.

13. The method of claim 11, wherein the first and second polymeric coatings comprise a polysaccharide.

14. The method of claim 11, wherein the first and second polymeric coatings each comprises an alginate.

15. The method of claim 14, wherein the alginate is selected from the group of guluronate alginate, mannuronate alginate, and combinations thereof.

16. The method of claim 15, wherein the first polymeric coating comprises a mixture of guluronate alginate and mannuronate alginate in a ratio of greater than about 50:50 and the second polymeric coating comprises a mixture of mannuronate alginate to guluronate alginate in a ratio of greater than about 50:50.

17. The method of claim 11, wherein the liquid carrier comprises a saline solution.

18. The method of claim 11, wherein the atomizing and gelling of the suspension is accomplished by introducing the alginate suspension into a center cup of a spinning disk encapsulation apparatus having an outer collection chamber containing a gelling solution.

19. The method of claim 18, wherein the center cup of the spinning disk encapsulation apparatus includes at least one groove defined on an inner wall of the center cup and wherein the introducing of the suspension into the center cup causes droplets to travel from the center cup into the outer collection chamber in one or more relatively well-defined singulated lines.

20. The method of claim 11, further comprising agitating the second polymeric coating composition as the flowing stream of droplets is introduced.

21. A method of encapsulating cell clusters of biological material comprising:

suspending cell clusters of biological material in a first alginate solution to form a first alginate suspension;

forming droplets of the first alginate suspension, at least some of the droplets containing at least one of the cell clusters;

gelling the droplets of the first alginate suspension to form single-coated capsules having a first layer coating surrounding at least a portion of each of the droplets;

suspending the single-coated capsules in a liquid carrier medium to form a carrier suspension;

applying an electrostatic charge to the carrier suspension prior to introducing the carrier suspension as a singulated flowstream into a second alginate solution to create a second alginate suspension;

forming droplets of the second alginate suspension, at least some of the droplets containing at least one of the single-coated capsules; and gelling the droplets of the second alginate suspension to form a second layer coating surrounding the single-coated capsules.

22. The method of claim 21, wherein the forming of the droplets of both the first and second alginate suspension is accomplished by introducing the alginate suspension into a center cup of a spinning disk encapsulation apparatus having an outer collection chamber containing a gelling solution.

23. The method of claim 22, wherein the center cup of the spinning disk encapsulation apparatus includes at least one groove defined on an inner wall of the center cup such that introducing the alginate suspension into the center cup causes the separated capsules to travel from the center cup into the outer collection chamber in one or more singulated lines.

24. The method of claim 21, wherein the method if performed for a single batch of at least one hundred thousand cell clusters in a total time of less than three hours.

25. The method of claim 24, the carrier medium is low viscosity liquid physiologically balanced for the biological material.

26. The method of claim 21, wherein the method is used to double-encapsulate all of the biological material from a donor organ in a single pass through the method.

27. The method of claim 21, further comprising the step of agitating the second alginate solution as the flowstream of carrier medium containing the single-coated capsules is introduced into second alginate solution.

28. The method of claim 21, wherein the cell clusters comprise pancreatic islets.

29. The method of claim 21, wherein the first alginate solution comprises a mixture of guluronate alginate and mannuronate alginate in a ratio of greater than about 50:50 and the second alginate solution comprises a mixture of mannuronate alginate to guluronate alginate in a ratio of greater than about 50:50.

30. The method of claim 21, further comprising the step of:
 processing the single-coated capsules prior to suspending the single-coated capsules in the liquid carrier medium by exposing the single-coated capsules to at least one low concentration formulation of a gelling solution for a period of less than about 30 minutes.

* * * * *